(12) United States Patent
Karam et al.

(10) Patent No.: US 9,685,174 B2
(45) Date of Patent: Jun. 20, 2017

(54) MOOD MONITORING OF BIPOLAR DISORDER USING SPEECH ANALYSIS

(71) Applicant: THE REGENTS OF THE UNIVERSITY OF MICHIGAN, Ann Arbor, MI (US)

(72) Inventors: Zahi N. Karam, Ann Arbor, MI (US); Satinder Singh Baveja, Ann Arbor, MI (US); Melvin Mcinnis, Ann Arbor, MI (US); Emily Mower Provost, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/702,215

(22) Filed: May 1, 2015

(65) Prior Publication Data
US 2015/0318002 A1    Nov. 5, 2015

Related U.S. Application Data

(60) Provisional application No. 61/987,871, filed on May 2, 2014.

(51) Int. Cl.
*G10L 15/00* (2013.01)
*G10L 25/00* (2013.01)
(Continued)

(52) U.S. Cl.
CPC .............. *G10L 25/66* (2013.01); *A61B 5/165* (2013.01); *A61B 5/4803* (2013.01);
(Continued)

(58) Field of Classification Search
None
See application file for complete search history.

(56) References Cited

U.S. PATENT DOCUMENTS

2009/0270170 A1    10/2009  Patton
2009/0313019 A1*   12/2009  Kato ................ G10L 17/26
                                                   704/254
(Continued)

FOREIGN PATENT DOCUMENTS

KR    2008-0086791 A    9/2008

OTHER PUBLICATIONS

Survey paper on depression: Cummins, Nicholas, Stefan Scherer, Jarek Krajewski, Sebastian Schnieder, Julien Epps, and Thomas F. Quatieri. "A review of depression and suicide risk assessment using speech analysis." Speech Communication 71 (Jul. 2015): 10-49.
(Continued)

*Primary Examiner* — Marcus T Riley
(74) *Attorney, Agent, or Firm* — Marshall, Gerstein & Borun LLP (57) ABSTRACT

A system that monitors and assesses the moods of subjects with neurological disorders, like bipolar disorder, by analyzing normal conversational speech to identify speech data that is then analyzed through an automated speech data classifier. The classifier may be based on a vector, separator, hyperplane, decision boundary, or other set of rules to classify one or more mood states of a subject. The system classifier is used to assess current mood state, predicted instability, and/or a change in future mood state, in particular for subjects with bipolar disorder.

20 Claims, 4 Drawing Sheets

(51) Int. Cl.
*G10L 25/66* (2013.01)
*G10L 25/48* (2013.01)
*G10L 15/22* (2006.01)
*G10L 17/26* (2013.01)
*A61B 5/00* (2006.01)
*A61B 5/16* (2006.01)
*G10L 25/03* (2013.01)
*G10L 25/27* (2013.01)

(52) U.S. Cl.
CPC .......... *A61B 5/6898* (2013.01); *A61B 5/7246* (2013.01); *A61B 5/7264* (2013.01); *A61B 5/7267* (2013.01); *G10L 15/22* (2013.01); *G10L 17/26* (2013.01); *G10L 25/48* (2013.01); *G10L 25/03* (2013.01); *G10L 25/27* (2013.01)

(56) References Cited

U.S. PATENT DOCUMENTS

2010/0280336 A1* 11/2010 Giftakis ............... A61B 5/0476 600/301
2014/0046660 A1* 2/2014 Kamdar .................. G10L 25/63 704/235

OTHER PUBLICATIONS

Relevant patent: Quatieri, Thomas F., James R. Williamson, Brian Helfer, Rachelle Laura Horwitz-Martin, Bea Yu, and Daryush Dinyar Mehta. "Using correlation structure of speech dynamics to detect neurological changes." U.S. Appl. No. 14/518,490, filed Oct. 20, 2014.
Girard, Jeffrey M., and Jeffrey F. Cohn. "Automated Audiovisual Depression Analysis." Current Opinion in Psychology (Dec. 2014).
Bozkurt, Elif, Orith Toledo-Ronen, Alexander Sorin, and Ron Hoory. "Exploring modulation spectrum features for speech-based depression level classification." In Proceedings of the 15th Annual Conference of the International Speech Communication Association. Sep. 2014.
Senoussaoui, Mohammed, Milton Sarria-Paja, João F. Santos, and Tiago H. Falk. "Model fusion for multimodal depression classification and level detection." In Proceedings of the 4th International Workshop on Audio/Visual Emotion Challenge, pp. 57-63. ACM, Nov. 2014.
Cummins, Nicholas, Vidhyasaharan Sethu, Julien Epps, Sebastian Schnieder, and Jarek Krajewski. "Analysis of acoustic space variability in speech affected by depression." Speech Communication (Sep. 2015).
Cummins, Nicholas, Julien Epps, Vidhyasaharan Sethu, and Jarek Krajewski. "Weighted pairwise Gaussian likelihood regression for depression score prediction." In Acoustics, Speech and Signal Processing (ICASSP), 2015 IEEE International Conference on, pp. 4779-4783. IEEE, Apr. 2015.
Scherer, Stefan, Zakia Hammal, Ying Yang, Louis-Philippe Morency, and Jeffrey F. Cohn. "Dyadic behavior analysis in depression severity assessment interviews." In Proceedings of the 16th International Conference on Multimodal Interaction, pp. 112-119. ACM, Nov. 2014.
Gupta, Rahul, Nikolaos Malandrakis, Bo Xiao, Tanaya Guha, Maarten Van Segbroeck, Matthew Black, Alexandros Potamianos, and Shrikanth Narayanan. "Multimodal prediction of affective dimensions and depression in human-computer interactions." In Proceedings of the 4th International Workshop on Audio/Visual Emotion Challenge, pp. 33-40. ACM, Nov. 2014.
Alghowinem et al., Characterising depressed speech for classification, INTERSPEECH 2013, 5 pp. (Jan. 2013).
Ben-Zeev et al., Next-generation psychiatric assessment: using smartphone sensors to monitor behavior and mental health, Psychiatric Rehabilitation Journal, 38(3):218-26 (Sep. 2015).
Bone et al., Spontaneous-speech acoustic-prosodic features of children with autism and the interacting psychologist, INTERSPEECH 2012 Conference, 4 pp. (Sep. 2012).
Chaspari et al., Analyzing the structure of parent-moderated narratives from children with ASD using an entity-based approach, INTERSPEECH 2013 Conference, pp. 2430-2434 (Aug. 2013).
Choudhury et al., Intraoperative round window recordings to acoustic stimuli from cochlear implant patients, Otol. Neurotol., 33(9):1507-15 (Dec. 2012).
Cohn et al., Detecting depression from facial actions and vocal prosody, 3rd International Conference on Affective Computing and Intelligent Interaction (ACII), 7 pages (Apr. 2009).
Cummins et al., Modeling spectral variability for the classification of depressed speech, INTERSPEECH Conference 2013: 5 pages (Aug. 2013).
Eyben et al., openSMILE—The Munich versatile and fast open-source audio feature extractor, MM'10 Conference, Firenze, Italy, pp. 1459-1462 (Oct. 2010).
Helfer et al., Classification of depression state based on articulatory precision, INTERSPEECH 2013 Conference, 5 pp. (Aug. 2013).
Hoque et al., Exploring speech therapy games with children on the autism spectrum, 10th Annual Conference of teh International Speech Communication Association, INTERSPEECH 2009, 5 pp. (Oct. 2009).
Karam et al., Ecologically valid long-term mood monitoring of individuals with bipolar disorder using speech, 2014 IEEE International Conference on Acoustics, Speech and Signal Processing (ICASSP), pp. 4858-4862 (May 2014).
Mower et al., A framework for automatic emotion classification using emotion profiles, IEEE Trans. Audio, Speech, Language Processing, 19(5):1057-70 (Jul. 2011).
Mundt et al., Voice acoustic measures of depression severity and treatment response collected via interactive voice response (IVR) technology, J. Neurolinguistics, 20(1):50-64 (Jan. 2007).
Oller et al., Automated vocal analysis of naturalistic recordings from children with autism, language delay, and typical development, Proc. Natl. Acad. Sci. USA, 107(30):13354-9 (Apr. 2010).
Tokuno et al., Usage of emotion recognition in military health care, Defense Science Research Conference and Expo (DSR): 1-5, IEEE (Aug. 2011).
Van den Broek et al., Telling the story and re-living the past: how speech analysis can reveal emotions in post-traumatic stress disorder (PTSD) patients, Chapter 10 in: Westerink et al. (eds.), Sensing Emotions, Philips Research Book Series 12, Springer Science+Business Media B.V. (Jul. 2011).
van der Sluis et al., Towards an artificial therapy assistant, HEALTHINF 2011—International Conference on Health Informatics, pp. 357-363 (Jan. 2011).
van Santen et al., Computational prosodic markers for autism, Austism, 14(3):215-36 (May 2010).
International Search Report for International application No. PCT/US2015/028863, mailed Aug. 27, 2015.
Written Opinion for International application No. PCT/US2015/028863, mailed Aug. 27, 2015.
Sturim et al, Automatic Detection of Depression in Speech Using Gaussian Mixture Modeling with Factor Analysis, INTERSPEECH 2011, pp. 2981-2984. 4 pp. (Aug. 2011 (http://www.isca-speech.org/archive/interspeech_20/1/i11_2981.html).
Abdullah et al., Towards Circadian Computing: How "Early to Bed and Early to Rise" Makes Some of Us Unhealthy and Sleep Deprived. Proceedings of Ubicomp (Sep. 13-17, 2014).
Abdullah et al., Towards Population Scale Activity Recognition: A Scalable Framework for Handling Data Diversity. Proceedings of AAAI 2012 (Jul. 2012).
Adams et al., Towards Personal Stress Informatics: Comparing Minimally Invasive Techniques for Measuring Daily Stress in the Wild. Proceedings of the International Conference on Pervasive Computing Technologies for Healthcare 2014.
Augustine et al., A positivity bias in written and spoken English, and its moderation by personality and gender. Social Psychology and Personality Science, 2(5):508-15 (2011).

(56) References Cited

OTHER PUBLICATIONS

Basu et al., Towards Measuring Human Interactions in Conversational Settings. Proceedings of Computer Vision and Pattern Recognition (Cues in Communication) (Dec. 2001).
Berke et al., Objective Sensing of Activity and Sociability: Mobile Sensing in the Community. Annals of Family Medicine, vol. 9, Issue 4, pp. 344-350 (Jul. 2011).
Brown et al., Recall of expressed affect during naturalistically observed interpersonal events in those with Borderline Personality Disorder or Depressive Disorder. Assessment, 21, 72-80 (2014).
Campbell et al., From Smart Phones to Cognitive Phones. IEEE Pervasive, vol. 11, Issue 3, pp. 7-11 (Jul.-Sep. 2012).
Campbell et al., NeuroPhone: Brain-Mobile Phone Interface Using a Wireless EEG Headset. Proceedings of MobiHeld (2010).
Chang et al., Analyze This: unobtrusive mental health monitoring by voice, CHI EA '11, Extended Abstracts on Human Factors in Computing Systems, pp. 1951-1956 (2011).
Chang, Speech Analysis Methodologies towards Unobtrusive Mental Health Monitoring, Technical Report No. UCB/EECS-2012-55 (May 1, 2012).
Chen et al., Unobtrusive Sleep Monitoring Using Smartphones. Proceedings of Pervasive Health (2013).
Choudhury et al., Assessing Wellness by Sensing Everyday Activities and Interactions. Workshop Proceedings HCI Challenges in Health Assessment, Conference on Human Factors in Computing Systems (CHI), Portland, Oregon (Apr. 2005).
Choudhury et al., Boosting and Structure Learning in Dynamic Bayesian Networks for Audio-Visual Speaker Detection. Proceedings of International Conference on Pattern Recognition (Aug. 2002).
Choudhury et al., Characterizing Social Networks using the Sociometer. Proceedings of the North American Association of Computational Social and Organizational Science (Jun. 2004).
Choudhury et al., Learning Communities: Connectivity and Dynamics of Interacting Agents. Proceedings of the International Joint Conference on Neural Networks (Jul. 2003).
Choudhury et al., Modeling Conversational Dynamics as a Mixed Memory Markov Process. Advances of Neural Information Processing Systems 17 (NIPS 2004), MIT Press (2005).
Choudhury et al., Modeling Face-to-Face Communication using the Sociometer. Workshop Proceedings of Ubicomp 2003 (Workshop: Supporting Social Interaction and Face-to-face Communication in Public Spaces) (Oct. 2003).
Choudhury et al., Motion Field Histograms for Robust Modeling of Facial Expressions. Proceedings of International Conference on Pattern Recognition (Sep. 2000).
Choudhury et al., Multimodal Person Recognition Using Unconstrained Audio and Video. Second Conference on Audio- and Video-based Biometric Person Authentication (AVBPA 1999) (Mar. 1999).
Choudhury et al., Sensing and Modeling Human Networks Using the Sociometer. Proceeding of the International Conference on Wearable Computing (Oct. 2003).
Choudhury et al., The Sociometer: A Wearable Device for Understanding Human Networks. In the Workshop Proceedings of Computer Supported Cooperative Work (Workshop: Ad hoc Communications and Collaboration in Ubiquitous Computing Environments) (Nov. 2002).
Choudhury et al., Towards Activity Databases: Using Sensors and Statistical Models to Summarize People's Lives. IEEE Data Engineering Bulletin, vol. 29 No. 1, 8 pp. (Mar. 2006).
Choudhury et.al. The Mobile Sensing Platform: An Embedded System for Activity Recognition. IEEE Pervasive Computing Magazine—Special Issue on Activity-Based Computing (Apr. 2008).
Choudhury, FaceFacts—Study of Facial Features for Understanding Expressions. Master's thesis, Massachusetts Institute of Technology, Aug. 1999.
Choudhury, Sensing and Modeling Human Networks. Doctoral Thesis, Massachusetts Institute of Technology, Feb. 2004.

Harrison et al., Using Multi-modal Sensing for Human Activity Modeling in the Real World. Handbook of Ambient Intelligence and Smart Environments, Springer Verlag (2009).
Hasler et al., Preliminary evidence of diurnal rhythms in everyday behaviors associated with positive affect. Journal of Research in Personality, 42, 1537-1546 (2008).
Holleran et al., Eavesdropping on social life: The accuracy of stranger ratings of daily behavior from thin slices of natural conversations. Journal of Research in Personality, 43, 660-672 (2009).
Holleran et al., Talking shop and shooting the breeze: A study of workplace conversations and job disengagement among STEM faculty. Social Psychological and Personality Science, 2, 65-71 (2011).
Holtzman et al., Sounds like a narcissist: Behavioral manifestations of narcissism in everyday life. Journal of Research in Personality, 44, 478-484 (2010).
Klasjna et al., Exploring Privacy Concerns about Personal Sensing. Proceedings of Pervasive Computing, Nara, Japan (May 2009).
Lane et al., A Survey of Mobile Phone Sensing. IEEE Communications (Sep. 2010).
Lane et al., BeWell: A Smartphone Application to Monitor, Model and Promote Wellbeing, Pervasive Health 2011—5th International ICST Conference on Pervasive Computing Technologies for Healthcare, Dublin, Ireland (May 23-26, 2011).
Lane et al., Community Similarity Networks, Journal of Personal and Ubiquitous Computing (May 22, 2013).
Lane et al., Cooperative Communities (CoCo): Exploiting Social Networks for Large-scale Modeling of Human Behavior. IEEE Pervasive Computing—Special Issue on Large-scale Opportunistic Sensing, pp. 45-53 (Oct.-Dec. 2011).
Lane et al., Enabling Large-scale Human Activity Inference on Smartphones using Community Similarity Networks. Proceedings of Ubicomp 2011, Beijing, China (Sep. 2001).
Lester et al., A Hybrid Discriminative-Generative Approach for Modeling Human Activities. Proceedings of International Joint Conference on Artificial Intelligence (IJCAI 2005), Edinburgh, Scotland (Jul. 2005).
Lester et al., A Practical Approach to Recognizing Physical Activities. Proceedings of Pervasive Computing, Dublin, Ireland (May 2006).
Lester et al., Choosing the Right Modalities and Features for Activity Recognition. NIPS Workshop on Multi-modal Signal Processing, NIPS 2004, Whistler, British Colombia (2004).
Lester et al., Sensing and Modeling Activities to Support Physical Fitness. Workshop Proceedings of Ubicomp 2005, Tokyo, Japan (Workshop: Monitoring, Measuring and Motivating Exercise: Ubiquitous Computing to Support Fitness) (Sep. 2005).
Liao et al., Training Conditional Random Fields using Virtual Evidence Boosting. Proceedings of International Joint Conference on Artificial Intelligence (IJCAI 2007), Hyderabad, India (Jan. 2007).
Lin et al., BeWell+: Multidimensional Wellbeing Monitoring with Community-guided with User Feedback adn Energy Optimization,. Proceedings of Wireless Health 2012 (Oct. 2012).
Lu et al., Sound Sense: Scalable Sound Sensing for People-Centric Applications on Mobile Phones. Proceedings of Mobisys 2009, Krakow, Poland (Jun. 2009).
Lu et al., StressSense: Detecting Stress in Unconstrained Acoustic Environments using Smartphones. Proceedings of Ubicomp 2012 (Sep. 2012).
Lu et al., The Jigsaw Continuous Sensing Engine for Mobile Phone Applications. Proceedings of SenSys'10 (2010).
Mandaviani et al., Fast and Scalable Training of Semi-Supervised CRFs with Application to Activity Recognition. Proceedings of NIPS 2007, Vancouver, Canada (Dec. 2007).
Matthews et al.,Tracking Mental Well-Being: Balancing Rich Sensing and Patient Needs. Computer, 47.4(2014).
Mehl et al., An empirical analysis of the obtrusiveness of and participants' compliance with the Electronically Activated Recorder (EAR). European Journal of Psychological Assessment, 23, 248-257 (2007).
Mehl et al., Are women really more talkative than men? Science, 317, 82 (2007).

(56) References Cited

OTHER PUBLICATIONS

Mehl et al., Eavesdropping on happiness: Well-being is related to having less small talk and more substantive conversations. Psychological Science, 21, 539-541 (2010).
Mehl et al., Naturalistic observation of health-relevant social processes: The Electronically Activated Recorder (EAR) methodology in psychosomatics. Psychosomatic Medicine, 74, 410-417 (2012).
Mehl et al., Naturalistic observation sampling: The Electronically Activated Recorder (EAR). In M. R. Mehl & T. S. Conner (Eds.), Handbook of research methods for studying daily life. New York, NY: Guilford Press (2012), found at <https://books.google.com/books?id=oseYAwAAQBAJ&lpg=PA176&ots=K-2QfuQrWK&dq=Naturalistic%20Observation%20Sampling%3A%20The%20Electronically%20Activated%20Recorder&pg=PA175#v=onepage&q=Naturalistic%20Observation%20Sampling:%20The%20Electronically%20Activated%20Recorder&f=false <https://books.google.com/books?id=oseYAwAAQBAJ&lpg=PA176&ots=K-2QfuQrWK&dq=Naturalistic%20Observation%20Sampling%3A%20The%20Electronically%20Activated%20Recorder&pg=PA175>.
Mehl et al., The social dynamics of a cultural upheaval: Social interactions surrounding Sep. 11, 2001. Psychological Science, 14, 579-585 (2003).
Mehl et al.,The sounds of social life: A psychometric analysis of students daily social environments and natural conversations. Journal of Personality and Social Psychology, 84, 857-870 (2003).
Mehl, Eavesdropping on health: A naturalistic observation approach for social-health research. Social and Personality Psychology Compass, 1, 359-380 (2007).
Mehl, Naturalistic observation of daily behavior in personality psychology [Comment on Furr's target article]. European Journal of Personality, 23, 414-416 (2009).
Mehl, Personality in its natural habitat: Manifestations and implicit folk theories of personality in daily life. Journal of Personality and Social Psychology, 90, 862-877 (2006).
Mehl, The lay assessment of sub-clinical depression in daily life. Psychological Assessment, 18, 340-345 (2006).
Miluzzo et al., Darwin Phones: The Evolution of Sensing and Inference on Mobile Phones. Proceedings of MobiSys 2010, San Francisco, CA (Jun. 2010).
Munguia-Tapia et al., Building Reliable Activity Models using Hierarchical Shrinkage and Mined Ontology. Proceedings of Pervasive Computing, Dublin, Ireland (May 2006).
Musolesi et al., The Second Life of a Sensor: Integrating Real-world Experience in Virtual Worlds using Mobile Phones, Proceedings of Fifth Workshop on Embedded Networked Sensors (HotEmNets 2008), Charlottesville, Virginia (Jun. 2008).
Palmier-Claus et al., Integrating mobile-phone based assessment for psychosis into people's everyday lives and clinical care: a qualitative study, BMC Psychiatry, 13:34 (2013).
Peebles et al., Community-Guided Learning: Exploiting Mobile Sensor Users to Model Human Behavior. Proceedings of AAAI 2010, Atlanta, Georgia, (Jul. 2010).
Pentland et al., Face Recognition for Smart Environments. IEEE Computer Magazine, 33(2):50-55 (Feb. 2000).
Pentland et al., Human Dynamics: Computation for Organization. Pattern Recognition Letters, vol. 26, Issue 4, pp. 503-511 (Mar. 2005).
Prociow et al., Mobile psychiatry: towards improving the care for bipolar disorder, Int. J. Mental Health Systems, 6:5 (2012).
Prociow et al., Towards personalised ambient monitoring of mental health via mobile technologies, Technol. Health Care, 18(4-5):275-84 (2010).
Rabbi et al., Passive and In-situ Assessment of Mental and Physical Well-being using Mobile Sensors. Proceedings of Ubicomp 2011, Beijing, China (Sep. 2011).
Rahman et al., BodyBeat: A Mobile System for Sensing Non-Speech Body Sounds. Proceedings of the International Conference on Mobile Systems, Applications, and Services (MobiSys) 2014.
Rahman et al., Towards Accurate Non-Intrusive Recollection of Stress Levels Using Mobile Sensing and Contextual Recall. Proceedings of the International Conference on Pervasive Computing Technologies for Healthcare (2014).
Ramirez-Esparza et al., Are Mexicans more or less sociable than Americans? Insights from a naturalistic observation study. Journal of Research in Personality, 43, 1-7 (2009).
Robbins et al., Cancer conversations in context: Naturalistic observation of couples coping with breast cancer. Journal of Family Psychology (In Press).
Robbins et al., Naturalistically observed sighing and depression in rheumatoid arthritis patients: A preliminary study. Health Psychology, 30, 129-133 (2011).
Robbins et al., Naturalistically observed swearing, emotional support and depressive symptoms in women coping with illness. Health Psychology, 30, 789-792 (2011).
Snyder et al., Making Things Visible: Opportunities and Tensions in Visual Approaches for Design Research. Human-Computer Interaction, vol. 29, 2014, Issue 5-6, pp. 451-486 (2014).
Sohn et al., Mobility Detection Using Everyday GSM Traces. Proceedings of Ubicomp 2006, Orange County, California (Sep. 2006).
Sriram et al., Activity-aware ECG-based Patient Authentication for Remote Health Monitoring. Proceedings of the International Conference on Multi-Modal Interfaces (ICMI-MLMI) 2009, Cambridge, Massachusetts (Nov. 2009).
Tanzeem Choudhury, Associate Professor, Information Science, Cornell University, Publications List, http://www.cs.cornell.edu/~tanzeem/pubs/pubs.html.
Tenney et al., This examined life: The upside of self-knowledge for interpersonal relationships. PLoS ONE, 8, e69605 (2013).
The Electronically Activated Recorder, downloaded from the Internet at: <http://dingo.sbs.arizona.edu/~mehl/EAR.htm>.
Tomko et al., Social context of anger in Borderline Personality Disorder and Depressive Disorders: Findings from a naturalistic observation study. Journal of Personality Disorders (2012).
Vazire et al., Knowing me, knowing you: The relative accuracy and unique predictive validity of self- and other ratings of daily behavior. Journal of Personality and Social Psychology, 95, 1202-1216 (2008).
Voida et al., Personal Informatics Can Be Stressful: Collecting, Reflecting, and Embedding Stress Data in Personal Informatics. Proceeding of Personal Informatics Workshop, CHI'13 (Apr. 27-May 2, 2013).
Wang et al., Commonsense-based Joint Training of Human Activity Recognizers. Proceedings of International Joint Conference on Artificial Intelligence (IJCAI 2007), Hyderabad, India (Jan. 2007).
Wu et al., a Scalable Approach to Activity Recognition Based on Object Use. Proceedings of ICCV 2007, Rio de Janeiro, Brazil (Oct. 2007).
Wyatt et al., A Privacy Sensitive Approach to Modeling Multi-Person Conversations. Proceedings of International Joint Conference on Artificial Intelligence (IJCAI 2007), Hyderabad, India (Jan. 2007).
Wyatt et al., Capturing Spontaneous Conversation and Social Dynamics: A Privacy-Sensitive Data Collection Effort. Proceedings of International Conference on Acoustics, Speech, and Signal Processing (ICASSP 2007), Honolulu, HI (Apr. 2007).
Wyatt et al., Conversation Detection and Speaker Segmentation in Privacy Sensitive Situated Speech Data. Proceedings of Interspeech 2007, Antwerp, Belgium (Aug. 2007).
Wyatt et al., Discovering Long Range Properties of Social Networks with Multi-Valued Time-Inhomogeneous Models. Proceedings of AAAI 2010, Atlanta, Georgia (Jul. 2010).
Wyatt et al., Dynamic Multi-Valued Network Models for Predicting Face-to-Face Conversations. NIPS Workshop on Analyzing Networks and Learning with Graphs, Whistler, British Columbia, (Dec. 2009).
Wyatt et al., Inferring Colocation and Conversation Networks from Privacy-senstive Audio with Implications for Computational Social Science. ACM Transactions on Intelligent Systems and Technology, vol. 1, Issue 2 (Jan. 2011).

(56) References Cited

OTHER PUBLICATIONS

Wyatt et al., Learning Hidden Curved Exponential Random Graph Models to Infer Face-to-Face Interaction Networks from Situated Speech Data. Proceedings of AAAI 2008, Chicago, Illinois (Jul. 2008).

Wyatt et al., Towards Automated Social Analysis of Situated Speech Data. Proceedings of Ubicomp 2008, Seoul, South Korea (Sep. 2008).

Wyatt et al., Unsupervised Activity Recognition Using Automatically Mined Common Sense. Proceedings of the Twentieth National Conference on Artificial Intelligence (AAAI 2005), Pittsburgh, Pennsylvania (Jul. 2005).

* cited by examiner

MOOD MONITORING OF BIPOLAR DISORDER USING SPEECH ANALYSIS

CROSS REFERENCE TO RELATED APPLICATION

This application claims the benefit of U.S. Provisional Patent Application No. 61/987,871 entitled "Mood Monitoring Of Bipolar Disorder Using Speech Analysis," filed May 2, 2014, the disclosure of which is hereby expressly incorporated by reference in its entirety.

STATEMENT OF GOVERNMENTAL INTEREST

This invention was made with government support under MH100404 and TR000433 awarded by the National Institutes of Health. The Government has certain rights in the invention.

FIELD OF THE INVENTION

The present disclosure relates to assessing patients with speech-identifiable disorders and, more particularly, to monitoring mood of patients with bipolar disorder through speech analysis.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Bipolar disorder (BP) is a common and severe psychiatric illness characterized by pathological swings of mania and depression and is associated with devastating personal, social, and vocational consequences (suicide occurs in up to 20% of cases, by some reports). Bipolar disorder is among the leading causes of disability worldwide. The cost in the United States alone was estimated at $45 billion annually (in 1991 dollars). These economic and human costs, along with the rapidly increasing price of health care provide the impetus for a major paradigm shift in health care service delivery, namely to monitor and prioritize care with a focus on prevention.

Speech patterns have been effectively used in clinical assessment for both medical and psychiatric disorders. Clinicians are trained to record their observations of speech and language, which become a critical component of the diagnostic process. Recently, there have been research efforts exploring computational speech analysis as a way to assess and monitor the mental state of individuals suffering from a variety of psychological illnesses, specifically major depression (MD), autism, and post-traumatic stress disorder (PTSD).

For example, stress and anxiety have been studied extensively and elements of speech have been correlated with subjectively reported stress in PTSD. Other research efforts have demonstrated the efficacy of speech-based assessments for autism focusing on diagnosis, in addition to predicting the course and severity of the illness. Variations in speech patterns have also been used for computational detection and severity assessment in major depressive disorder.

However, most work in these areas focuses on the assessment of participants over short periods of time, at most several weeks, rendering it challenging to measure the natural fluctuations that accompany illness trajectories. Additionally, the speech input is often highly structured and collected in controlled environments. This limitation in speech collection precludes an understanding of how acoustic patterns characteristic of natural speech variation correlate with mood symptomology.

SUMMARY

The present techniques provide for estimating the mood state (including affect) of individuals with neurological disorders, like bipolar disorder (BP). Bipolar disorder is characterized by fluctuating mood state, including periods of depression (lowered mood state), mania (elevated mood state), and euthymia (neither mania nor depression). We monitored patients over the course of six months to a year, using normal conversation analysis, to assess the dynamic nature of the symptoms of BP. In addition to mood state, the present techniques can identify, more broadly, the mental state or neurophysiological state of a subject associated with speech-identifiable conditions.

As we show, the techniques were successful in detecting the presence of mania and depression in normal, unobtrusive, and unstructured speech-based communications of individuals. We were able to assess the underlying mood of the individual from the speech collected. As described, the techniques, as applied, provide evidence that mood-related variations recorded both from structured and unstructured speech-based communications (e.g., cell phone conversation data) are reflective of underlying mood symptomology and that the acoustic variations indicative of mood patterns across these conversation types differ.

The present techniques are also able to highlight the features of the speech that are most correlated with the clinical assessment of manic and depressive mood states.

The techniques herein provide for longitudinal, ecological (e.g., with minimally added effort and fitting within the daily routine of the subject), and continuous collection of unstructured speech in diverse environments and in the acoustic analysis of the BP participant population that exhibit dimensional mood-states with two extremes of a continuous mood-state spectrum: depression and mania. These results show that this style of data collection can be effectively used, highlighting the potential for autonomous ecologically valid monitoring for mental health assessment.

In accordance with an example, a method of detecting a speech-identifiable condition of a subject, the method comprises: receiving speech data of the subject; performing, in a feature extraction module, a low-level feature extraction on the speech data over a plurality of short-time segments to develop low-level feature data; performing, in the feature extraction module, a statistical analysis of the low-level feature data over a window of time to develop segment-level feature data, where the window of time comprises the plurality of low-level feature time segments contained therein, and wherein the segment-level feature data is non-lexical data; applying the segment-level feature data to a decision module having a database of one or more classification rules, each classification rule corresponding to a different classification of the speech-identifiable condition; and determining, in the decision module, the classification of the speech-identifiable condition of the subject from the segment-level feature data.

In accordance with another example, a system to detect a speech-identifiable condition of a subject, the system comprises: a processor; a memory; a feature extraction module stored on the memory and adapted to cause the processor to, perform, on speech data, a low-level feature extraction over a plurality short-time segments to develop low-level feature data, and performing a statistical analysis of the low-level feature data over a window of time to develop segment-level feature data, where the window of time comprises the plurality of low-level feature time segments contained therein, and wherein the segment-level feature data is non-lexical data; and a decision module stored on the memory and adapted to cause the processor to, access a database of one or more classification rules, each classification rule corresponding to a different classification of the speech-identifiable condition; and determining the classification of the speech-identifiable condition of the subject from the segment-level feature data.

DETAILED DESCRIPTION

Described herein is a new framework for ecological long-term monitoring of mood states for individuals with bipolar disorder. The techniques provide ecological data collection that does not request subjects to interact in constrained clinical environments but rather monitors subjects during normal conversation. The techniques, unlike speech recognition (and related technologies), provide non-lexical monitoring and analysis of subjects. Speech data is analyzed over short-time windows and then a statistical analysis is applied that makes lexical reconstruction either extremely difficult or not available. This provides subjects with a level of privacy against speech (lexical) reconstruction, which may also allow for more natural speech for the subject and thus more accurate monitoring and assessment of mood state. This promotes more continuous use of the techniques, which allows for increased probability of predicting a mood shift, as the subject will be encouraged to use the technique all the time. The techniques here promote personalized classifiers of mood state, allowing subjects to have tailored monitoring and assessment of current and predicted future mood states. Moreover, the techniques are extensible to any number of speech-identifiable ailments and conditions.

More specifically, the techniques herein involve collecting speech data, using a collection paradigm and developing a classification rule (or vector or separator or hyperplane or decision boundary) or set of classification rules to classify one or more mood states of the subject providing that speech data. The classification rule may then be used to assess current mood state or, in some instances, predicted instability or a change in future mood state. The results, as we show for example subjects with bipolar disorder, demonstrate that mania, hypomania (i.e., a lower level of intensity of manic symptoms), and depression can be differentiated from euthymia using speech-based classifiers trained on both structured interactions (e.g., monitoring weekly clinical speech-based interactions) and unstructured (e.g., monitoring normal patient telephone calls) cell phone recordings. By assessing structured interactions to identify a patient's mood and labeling those moods, we demonstrate that the present techniques can produce classification rules that detect (or classifications that indicate) the presence of hypomania when performing speech-analysis of only unstructured data collected. Classification rules for mania, hypomania, and depression have been developed. The classification rule is an example of a classifier; and the techniques herein may be used to train classifiers more broadly.

EXAMPLE

Experimental Setup

In developing the assessment method and systems herein, we developed an acoustic database (termed UM-AD herein), which contains longitudinally collected speech from individuals diagnosed with bipolar disorder participating as part of a bipolar longitudinal study (the Prechter BP Longitudinal Study), which is a multi-year study that takes a multidimensional, biological, clinical, and environmental, approach to the study of bipolar disorder.

UM-AD includes speech data collected from six participants, four women and two men (average age 41±11.2) diagnosed with bipolar disorder type I and with a history of rapid cycling, characterized by 4 or more episodes per year of mania, hypomania, or depression. Participants are recruited from the BP longitudinal study and enrolled for 6 months to a year.

Figure 1:
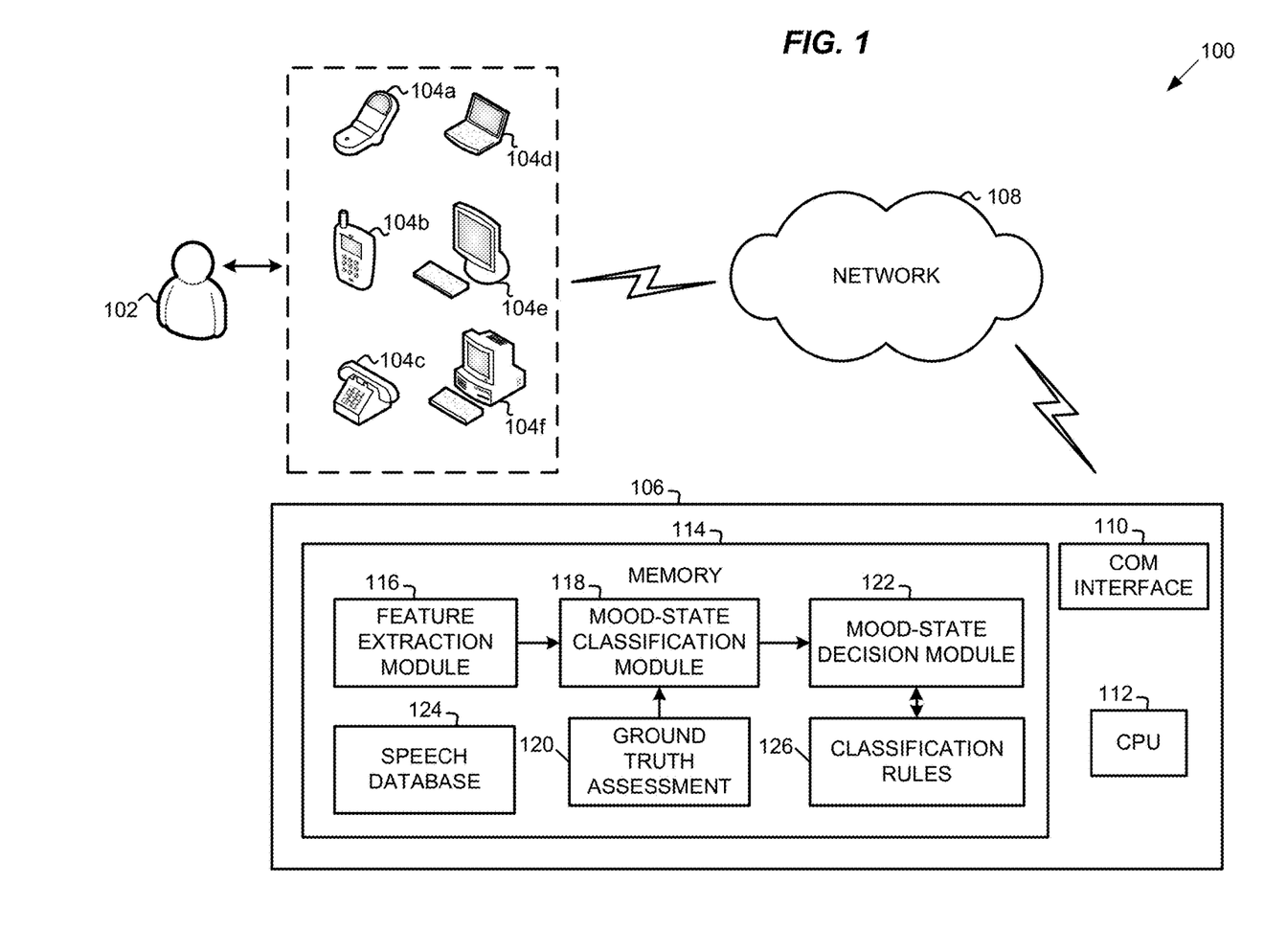
FIG. 1 illustrates an example system for mood detection that analyzes speech data from a subject and determines a subject's mood based on classifiers determined by or accessed by the system, in accordance with an example.

For the initial protocol, each participant was provided with a smart phone mobile device and an unlimited call/data plan for personal use and encouraged to use the phone as their primary mode of contact. While a smart-phone was used in the described example, the present techniques may be implemented through any speech-based device, whether involving conversational speech, between two people, or a device measuring speech of a single person, for example, talking into a recording device. The speech device may be self-contained, that is, performing recording, storage, and speech analysis. But in the examples detailed below, one or more of these operations (recording, storage, or analysis) is performed over distributed processing devices/systems connected to each other over a network, wired or wireless connection. Some example speech-based devices include are illustrated in FIG. 1.

In any event, for this discussed example, a smart phone was pre-loaded with an application (stored on a computer readable memory in the smart phone and executable by one or more processors therein) that instructs the smart phone to record only the participant's outgoing speech (i.e., no incoming speech is captured or recorded). The application automatically launches on the smart phone and runs persistently. The speech is stored on the smart phone at a recorded frequency, e.g., 8 KHz, and occurs whenever the participant makes or receives a phone call. The collected speech is then encrypted on the smart phone and securely transmitted over a network to an external processing system for analysis. The application, data transfer, and data handling followed strict security and encryption guidelines to ensure that the integrity and privacy of the collected data is not compromised.

During a training/testing protocol, weekly mood-state labels were determined for subjects. For example, ground truth measures of a participant's mood-state were obtained using weekly phone-based interactions with a clinician associated with this project. These interactions were structured (also termed constrained) and involved a clinician administering a twenty-minute recorded assessment that measured the mood-state of the participant over the past week. The assessments included the 17-item Hamilton Rating Scale for Depression (HAMD) as well as the Young Mania Rating Scale (YMRS) to assess the level of depression and mania, respectively. In the example experiment, no participant exhibited symptom severity associated with a manic episode. Therefore, for this particular implementation, detection of hypomania (elevated mood state not reaching the severity of mania) was the objective.

The mood assessment labels were categorized using thresholds set by the clinical team. The final labels were as follows: Hypomanic: YMRS>10 and HAMD<10. Depressed: HAMD>10 and YMRS<10. Euthymic: YMRS<6 and HAMD<6. Mixed: YMRS>10 and HAMD>10. The mixed mood-state was not included in this particular example, due to its rarity in the collected data.

The weekly clinical assessments ("evaluation call") provide a measure both of the participant's mood-state over the past week and of the clinician's perception of the participant's current (during evaluation call) mood-state. From this data, we sought to examine the hypothesis that the labels obtained during an evaluation call will be most strongly associated with the participant's mood during that evaluation call and thus with the mood-related modulations of the speech recorded during the call. We further sought to examine the hypothesis that the set of calls disjoint from the evaluation calls, i.e., the unstructured calls recorded outside of a clinical interaction, will possess a more subtle expression of mood symptomology, may involve masking of symptomology, but will, under our examination techniques, correlate (albeit less strongly) with the clinically assessed labels.

Statistics on Recorded Calls: A total of 221.2 hours was recorded from 3,588 phone calls. On average participants made 4.9±4.3 calls per day, with an average duration of 222.0±480.7 seconds and a median of 67.4 seconds.

The number of weeks of data available varied by participant: participant 1 had 31 weeks of data, while participant 5 had 6 weeks of data, for example. Each participant's data included euthymic weeks and at least one hypomanic and/or depressive week. Table 1 provides an overview of the collected data for each participant, showing the number of weeks of collected data with categorized assessment labels of euthymic, hypomanic, and depressive.

TABLE 1

Summary of collected data. #E, #H, #D are the number of weeks in Euthymic, Hypomanic, and Depressive states.

| | Part. # | | | | | |
|---|---|---|---|---|---|---|
| | 1 | 2 | 3 | 4 | 5 | 6 |
| #(E:H:D) | 22:2:7 | 9:0:4 | 21:1:3 | 10:9:1 | 2:4:0 | 3:0:4 |

The experiment sought to use the speech data collected in an unobtrusive manner and in unstructured environments to: (1) estimate the clinical assessment made during the participant-clinician weekly evaluation call; (2) determine the feasibility of detecting the mood state assessed during the evaluation call using unstructured personal cell phone (i.e., "smart phone") recordings from the same day as the evaluation call; and (3) apply this detection to cell phone recordings from days preceding or following the evaluation call. The experiment also conducted feature analyses to identify the speech features that are most informative for mood classification.

Datasets: The UM-AD dataset was partitioned based on proximity to evaluation call. Recall that the evaluation calls are the only recordings that are labeled. Further, the temporal consistency of mania and depression are variable and person dependent. Therefore, it was expected that the labels of the evaluation call are more strongly associated with calls recorded on the day of the evaluation as opposed to the day(s) before or after it.

The data was partitioned into the following disjoint datasets. Table 2 describes the per-participant summary of the number of calls assigned each of the three labels. The datasets include:

Evaluation calls: Speech collected during evaluation calls labeled as hypomanic/depressed/euthymic based on the clinical assessment.

Day-of calls: Speech collected from all calls recorded on the day of the clinical assessment, excluding the evaluation call.

Day before/after (B/A) calls: Speech collected from all calls made or received only on the adjacent day (before or after).

TABLE 2

Number of calls assigned each of the categorical labels:

| | | Part. # | | | | | |
|---|---|---|---|---|---|---|---|
| | | 1 | 2 | 3 | 4 | 5 | 6 |
| Eval | Euthymic | 18 | 8 | 21 | 6 | 1 | 2 |
| | Hypomanic | 2 | 0 | 1 | 3 | 3 | 0 |
| | Depressed | 6 | 4 | 3 | 1 | 0 | 3 |
| Day-Of | Euthymic | 52 | 227 | 127 | 11 | 10 | 17 |
| | Hypomanic | 13 | 0 | 5 | 14 | 11 | 0 |
| | Depressed | 22 | 114 | 21 | 1 | 0 | 22 |
| Day-B/A | Euthymic | 77 | 202 | 271 | 25 | 5 | 60 |
| | Hypomanic | 7 | 0 | 11 | 22 | 12 | 0 |
| | Depressed | 29 | 100 | 47 | 2 | 0 | 41 |

Training Methodology: The techniques included training classification algorithms based collected data, including the labels of the structured speech data. In this example implementation, the classification algorithms were trained using participant-independent modeling, capturing the variations associated with populations of individuals, rather than specific individuals. For the initial test of viability, the goal of participant-independent modeling was to understand how speech is modulated as a function of mood state while mitigating the effects of individual variability. We tested our models using the leave-one-participant-out cross-validation framework, where each participant is held out for testing and the remaining participants are used for training. The validation set is obtained using leave-one-training-participant out cross-validation within the training set. We trained the models using all data from the categories of euthymia, hypomania, and depression. We evaluated the performance of our depression and hypomania classifiers only for participants with at least two weeks of evaluation calls labeled as either depressed or hypomanic.

We protected the privacy of the participants given the sensitive nature of speech collected from personal phone calls. This was done through the use of statistics extracted from low-level audio features, rather than from using the features themselves. The statistics were calculated over windows of time longer than approximately 3 seconds, and in some examples from 3 seconds to 30 seconds, although the exact statistical window is not limited to this range. By applying a statistical window to our extraction and classification modeling, we developed a technique that obscured the lexical content of the original speech, rendering it extremely challenging to reconstruct the individual words. In some instances, reconstruction is not possible.

As discussed further below, we use a feature extraction module to extract low-level features. For example, in an implementation, we extracted 23 low-level features (LLF) using the openSMILE toolkit. For each recorded call, the speech data was first windowed into 25 ms frames overlapping by 15 ms, with the following (short-time) features extracted per frame:

Pitch, computed using the autocorrelation/cepstrum method, which yields the pitch over voiced windows. For unvoiced windows the pitch was set to 0. Whether a window was voiced was determined by a voicing probability measure, which we also include in the LLF.

RMS energy, zero-crossing rate, and the maximum and minimum value of the amplitude of the speech waveform.

Three voiced activity detection (VAD) measures: fuzzy, smoothed, binary. The fuzzy measure is computed using line-spectral frequencies, Mel spectra, and energy. The smoothed measure is the result of smoothing the fuzzy measure using a 10-point moving average. The binary measure is a 1/0 feature, determined by thresholding the fuzzy measure to assess presence of speech. The magnitude of Mel spectrum over 14 bands ranged from 50 Hz to 4 KHz.

The low-level (short time) (LLF) features include pitch, voicing probability, RMS energy, zero-crossing rate, max/min amplitude, fuzzy voiced activity detection (VAD), smoothed VAD, binary VAD, +14 features from 14 band Mel-spectrum.

From these low-level feature extractions, statistical extractions were performed (what we term segment-level feature extractions). The VAD measures and voicing probability provide an estimate of the location of speech and silence regions of the input speech waveform. We used these measures to group the speech into contiguous segments of participant speech ranging from 3 seconds to at most 30 seconds. We divided the call into segments by finding non-overlapping regions of at least 3 seconds. We first identified 3 consecutive frames whose energy, voicing probability, and fuzzy VAD were all above the $40^{th}$ percentile of their values over the whole call. We ended a segment when 30 consecutive frames had energy, voicing probability, and fuzzy VAD measures that fell below the $40^{th}$ percentile of their values over the whole call. If the segment length exceeded 30-seconds before reaching the stopping criteria, then the segment was ended and a new one started; this occurred for less than 3.5% of the segments. Each call had on average 24.3±46.6 segments with a median of 8.

We represented each segment by a 51-dimensional feature vector obtained from the statistics of the LLFs over the segment. This included 46 mean and standard deviation values of each LLF computed over the segment (for the pitch, these were computed only for frames with voiced speech), the segment length, and 4 segment-level features: relative and absolute jitter and shimmer measures. Each recorded call, $C_i$, is represented by $N_i$ feature vectors, where $N_i$ is the number of segments for call i.

Analysis of the segment-level features led to the development of classifier rules to determine the mood state of a subject. The classifier used in this example analysis was a support vector machine (SVM) with linear and radial-basis-function (RBF) kernels, implemented using LIBLINEAR and LIBSVM, respectively. The RBF kernel parameter was tuned over the range $\gamma \in \{0.0001, 0.001, 0.01, 0.1, 1\}$ on the participant-independent validation set. The regularization values were tuned for both the linear and RBF implementations over the set $C \in \{100, 10, 1, 0.1, 0.01\}$. The classifiers were trained on the segment-level 51-dimensional features.

For each test call ($C_i$), we independently classified each of its $N_i$ segments $s_{i,j}$ (j=1, . . . $N_i$). A test call could be either 1) a structured assessment call that is used to gather objective clinical assessment data for the purpose of establishing ground truth, or 2) an unstructured personal call that occurs "ecologically" in the course of daily life of the individual. For each segment, we calculated its signed distance to the hyperplane, $d_{i,j}$. We aggregated each distance into a vector $D_i$. The score for each call was associated with the $p^{th}$ percentile of $D_i$. The percentile was chosen using the validation set over the range $p \in \{10, 20, 30, 40, 50, 60, 70, 80, 90\}$.

The techniques demonstrated efficacy in differentiating between hypomanic and euthymic as well as depressed and euthymic speech using a participant-independent training, testing, and validation methodology. Performance was evaluated using the call-level area under the receiver operating characteristic curve (AUC).

Evaluation of Datasets: Table 3 presents the results across the three datasets. The results demonstrate that we are able to detect the mood state of individuals for calls recorded during the clinical interactions. For the first call type, i.e., the structured assessment call speech data, we obtained an average AUC of 0.81±0.17 in detecting hypomania and an average AUC of 0.67±0.18 in detecting depression across all participants.

We use two training scenarios for the calls recorded on the day of the evaluation and the days before/after the evaluation (the unstructured datasets): (1) classifier training using only the evaluation call dataset, testing on both unstructured datasets; and (2) classifier training over each unstructured dataset individually and testing with held out parts of the same dataset (e.g., training and testing on the day-of assessment calls). Method one asserts that the acoustic modulations that are indicative of mood state in the evaluation call will also be present in the unstructured calls, even if they are subtler. Method two asserts that even if the symptomology is present in the unstructured calls, the modulations may be different from those exhibited in the evaluation call. Therefore, in order to detect the mood state, the acoustic patterns in the unstructured data must be modeled directly. If the performance between methods one and two is similar, there is evidence for modulation consistency. If method two outperforms method one, there is evidence for modulation variability.

TABLE 3

Call-level AUC of binary mood-state classification. Train:Test indicates which dataset (Evaluation (Eval), Day-of (DOf), Day-B/A (BD/A)), was used for training and which for testing:

| Train:Test | Part. # | | | | | | $\mu \pm \sigma$ |
|---|---|---|---|---|---|---|---|
| | 1 | 2 | 3 | 4 | 5 | 6 | |
| Hypomanic vs Euthymic | | | | | | | |
| Eval: Eval | .78 | — | — | .67 | 1.0 | — | .81 ± .17 |
| Eval:DOf | .69 | — | — | .63 | .51 | — | .61 ± .09 |
| DOf:DOf | .66 | — | — | .50 | .79 | — | .65 ± .14 |
| Eval:DB/A | .48 | — | — | .52 | .43 | — | .47 ± .05 |
| DB/A:DB/A | .41 | — | — | .62 | .57 | — | .53 ± .11 |
| Depressed vs Euthymic | | | | | | | |
| Eval: Eval | .42 | .82 | .78 | — | — | .67 | .67 ± .18 |
| Eval:DOf | .49 | .60 | .43 | — | — | .43 | .49 ± .08 |
| DOf:DOf | .68 | .68 | .40 | — | — | .60 | .59 ± .13 |
| Eval:DB/A | .5 | .47 | .42 | — | — | .61 | .52 ± .09 |
| DB/A:DB/A | .50 | .52 | .53 | — | — | .34 | .52 ± .13 |

The results in Table 3 demonstrate that both method one and method two can be used to detect hypomania during the second call type data (i.e., unstructured personal calls) recorded on the day of the evaluation with an AUC of 0.61±0.09 and 0.65±0.14, respectively. The AUC for detecting depression was 0.49±0.08 and 0.59±0.13, for methods one and two, respectively. The results suggest that most individuals express mania and depression differently in clinical interactions compared to their personal life.

Most Informative Features: We examined the segment-level features that are most informative for classification using feature selection to further our understanding for how speech is affected by hypomanic and depressed mood states. To increase the robustness of the feature selection, we combined the two best performing datasets: evaluation calls and day-of calls, into a single set that contains all calls recorded on the day of the assessment. We performed feature selection using the leave-one-subject-out cross-validation paradigm using greedy forward feature selection for each of the hypomanic vs. euthymic and the depressed vs. euthymic classification problems. The selection only includes features that improve the average and minimum training participant segment-level AUCs and terminates when a further addition no longer yields improvement. The selected features were then used to train a classifier which was evaluated on the held out test participant.

The feature selection process yields different sets of features for each held out participant. Overall, the hypomanic vs. euthymic selection yields an average of 8.3±5.7 features and depressed vs. euthymic 5.2±4.0 features. Of the selected features, the segment-average of the binary VAD was common to all cross-validation folds for both hypomanic and depressed vs. euthymic. An additional three features were common to 3 out of 4 folds of hypomanic classification: standard deviation of the pitch, segment-average of the zero-crossing rate and of the smoothed VAD. While there were two additional features common to 3 of the 5 folds in the depressed classification: absolute jitter and the segment-average of the magnitude of Mel spectrum over the first band. Table 4 presents the resulting call-level AUCs for classifiers trained with only the selected features as well as those trained with all 51 features. The 51 segment-level features include mean of each of the LLF features, standard deviation of each of the LLF features, segment length, relative jitter, absolute jitter, relative shimmer, and absolute shimmer.

TABLE 4

Call-level AUC of binary mood-state classification using all features or only selected features:

| Train:Test | Part. # | | | | | | $\mu \pm \sigma$ |
|---|---|---|---|---|---|---|---|
| | 1 | 2 | 3 | 4 | 5 | 6 | |
| Hypomanic vs Euthymic | | | | | | | |
| All Feats | .61 | — | — | .37 | .84 | — | .61 ± .24 |
| Sel. Feats | .63 | — | — | .59 | .67 | — | .63 ± .04 |
| Depressed vs Euthymic | | | | | | | |
| All Feats | .62 | .65 | .42 | — | — | .65 | .59 ± .11 |
| Sel. Feats | .63 | .82 | .43 | — | — | .67 | .64 ± .16 |

The results demonstrate that with robust feature selection it is possible to separate euthymic speech from hypomanic and depressed mood states using on average approximately 5-8 segment-level features. Thus, feature selection improves our ability to detect depression, while reducing the variance across participants in the detection of hypomania, and thus improves the classification rules we develop.

The feature selection results highlight the importance of the average binary VAD for the detection of hypomanic and depressed moods. The mean binary VAD is correlated with the vocalization/pause ratio measure, which has been shown to be lower for depressed speech. Our examination of this measure showed a similar pattern for depressed speech, and also that it tends to be higher for hypomanic speech: we do this by first removing all instances of the feature ≥90% since a majority of the segments tend to be significantly voiced regardless of the label, and find that the feature is lowest for depressed (median(M)=0.51$\mu \pm \sigma$=0.46±0.32), higher for euthymic (M=0.63$\mu \pm \sigma$=0.52±0.33), and the highest for hypomanic (M=0.76$\mu \pm \sigma$=0.69±0.21).

As we show, the techniques provide a cost effective way to collect and scale continuous, unobtrusive speech data, from which the techniques monitor and assess mood of a subject. We can analyze non-clinical speech data, i.e., normal phone calls of a subject. In the discussed examples, subjects with bipolar disorder were examined, and different rules for mood states for hypomania, mania, and depression were developed. However, the above implementations are provided by way of example. The present techniques may be implemented in other ways and to identify any number of speech-affected conditions using rules based or other classifiers. Moreover, classification rules are developed for determining mood states in these examples; however, the classification rules may be to detect any number of states of health of patient. Such detections can be affected from using one or both of a low-level and segment-level feature extraction and analysis. The present techniques are extensible and may be used to develop classification rules for other conditions, including psychiatrically diagnosed conditions, pain, depression, physical conditions such as asthma, congenital heart disorders, coughing, lung related disorders, lung cancer, oncological disorders, grave's disease, hearing impairment, neuromuscular disorders, and neurological disorders.

The techniques can be used to produce a personalized signature, as a classification rule tailored for each subject. The techniques operate from statistical analysis over long chronological periods of very short time-interval measurements. In this way, the techniques may be lexicon-neutral—they don't need a patient to speak specific words or words at all. Classification rules can look at private, non-lexical speech data, from statistical measures over longer windows of time of features extracted from miniature milliseconds of filtered speech within that window. The techniques can monitor and assess changes in speech over the window periods of time, without doing any speech recognition or short-time speech pattern matching and lexical information analysis. And the techniques are able to do this from ecological speech data, i.e., collected during normal speech and daily life of the subject.

The techniques allow for near real time predictions of current mood state and can be used to predict the onset of changes in mood state with suitable classification rules developed from the speech data. This ability to predict mood onset can be used to flag health care providers and subjects themselves (and family and friends) when their speech data from normal conversations suggests that a change in mood is approaching, whether at that moment, an hour into the future, a day, several days, or otherwise.

FIG. 1 illustrates an example system 100 for mood detection of a subject 102. In the illustrated example, the subject 102 is described as having diagnosed bipolar disorder, although the system may be used to detect mood and other speech-identifiable condition state for any subject. The subject 102 communicates via speech through a communication device 104 that is adapted to collect and store speech data, for communication to a mood detection machine 106, through a network 108. The communication device 104 may be a cellular or mobile phone 104a, smart phone 104b, or landline telephone 104c. In other examples, the device 104 may be a laptop computer 104d or desktop computer 104e, 104f, with speech collection capabilities, e.g., a microphone. The device 104 may store the speech data and encrypt that speech data, e.g., using a public-key encryption protocol, before transmitting it to the detection machine 106.

The mood detection machine 106 contains a communication interface 110 for communicating over the network 108 and collecting speech data collected from the device 104. The machine 106 further includes a central processing unit 112 for executing instructions such as those from applications stored on a memory 114. The memory 114 includes a feature extraction module 116, a mood-state classification module 118, ground truth module 120, and mood-state decision module 122. The memory further includes a speech data memory 124 that stores received speech data from the device 104, such as, for example, structure and unstructured voice call recordings. The recordings can be created at the device 104 and transmitted over the network 108 to the machine 106; while in other examples, such as for analysis of real time phone calls, speech (i.e., voice) data may be received at the communication interface 110 continuously during a conversation, albeit preferably still by using encryption to deliver the data in real time. From here, the module 116 may store, in real time, the received speech data in the memory 124. In some examples the machine 106 and the device 104 may be integrated as part of a single device. For example, all recording, feature extraction, and classification processes herein may be performed on a smart phone.

Figure 2:
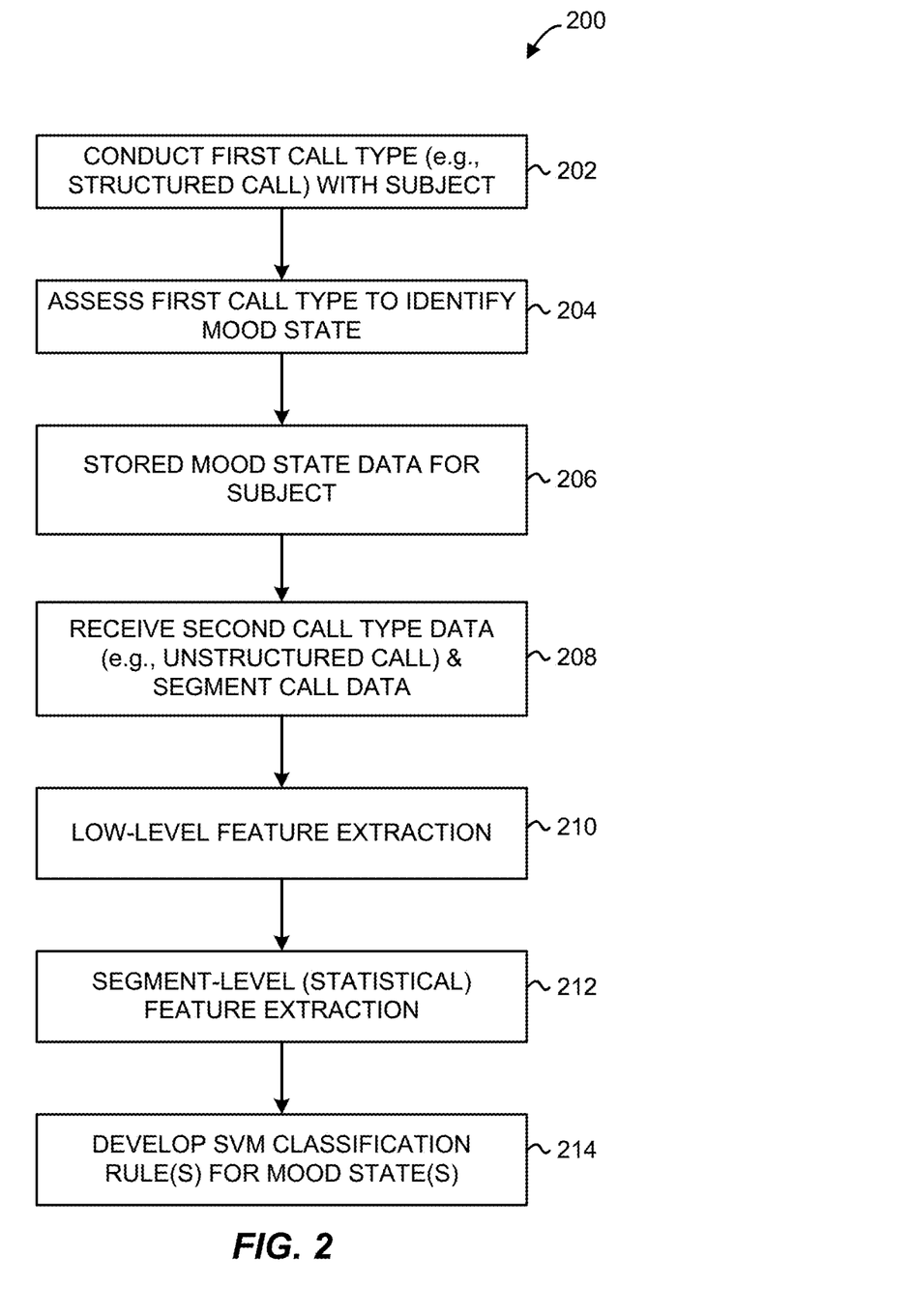
FIG. 2 illustrates a process, implemented by the system of FIG. 1, to develop classifiers (i.e., classification rules) for analyzing speech data.

FIG. 2 illustrates a process 200 that may be implemented by the system 100 of FIG. 1, specifically in a training example, where the system 100 is developing classification rules to be applied to ecological speech data. The process 200 includes a training procedure by which a first call type is used and assessed to determine a baseline mood state correlating to collected speech data, i.e., the mood state for the subject 102 with BP. At a block 202, the process 200 begins by conducting the first call type. This call may be a voice call where the speech of the participant is examined in a structured (i.e., constrained) environment, meaning an environment in which the nature of the call and at least some of what is discussed or elicited is established in a pre-structured manner, by a health care professional or other professional charged with assisting in the direct examination of the subject 102. The block 202 may be implemented by the subject 102 calling in to a professional using the device 104, where the professional is connected to the network 108 separately or through the machine 106. When a structured call, the first call type will be designed to allow the professional sufficient data to assess the mood state. For example, the structured call may be set to a predetermined minimum length, may include a structured conversation, questions/answers, uttering a given phrase, using a long set of vowels, etc. to allow for assessment.

While a call is illustrated (at the block 202), instead the speech may be from direct, in-person interaction between the subject and the professional, for example, having the subject 102 visit the offices of the professional using the machine 106.

In any event, at a block 204, the process 200 enters into a baselining procedure, where the process 200 determines a ground truth or initial mood state of the individual. For example, at the block 204, the process 200 may assess a first call to identify a mood state of the subject. This may occur in a completely manual process, with the professional making an objective determination of mood state from their professional experience in assessing speech patterns and making such diagnoses. In other examples, the block 204 may be implemented in a partially manual and partially automated manner, for example, with the professional collecting speech information and providing some guidelines to a detection system (such as the system 106) that then determines the mood state based on the speech data and the professional's input. In yet other examples, the block 204 may be implemented entirely automatically, as occurs with the block 214 described further below. In the example of ground truth, the mood state data can be obtained by short messaging service (SMS) or email questionnaire or through an application on the device 104, e.g., that shows different pictures and asks which picture best represents how the subject feels.

The ground truth assessment module 120 assesses the first call type and provides an identified mood state (e.g., for bipolar subjects—depression (lowered mood state), and hypomania (elevated mood state)) to the mood-state classification module 118 which stores the identified mood state. The ground truth assessment may be from an expert assessment, self-assessment of the subject, from a hospitalization assessment of the subject, or otherwise.

The blocks 202-206 provide a baselining portion of a training mode of the process 200.

Later, a second call type data is received at a block 208. This call type data can result from an actual phone call, i.e., with the subject 102 using the device 104 and calling over the network 108. Such data may be received real time, where the system device 104 is adapted to monitor, record, and transmit over the network 108 the speech of the subject 102 in real time. The call data may be speech data stored on the device 104 and encrypted and sent to the machine 106 at period times or in response from polling from the machine, either automatically in response to polling or after the device receives the polling request, notifies the subject, and the subject authorizes transmission. The call data may result from an evaluation call or a personal call of the subject.

In any event, the device 104 may be adapted to send only the speech of the subject 102 and not that of the other person (or persons) on the telephone call with the subject. This will not only avoid privacy concerns, and some limitations against recording of others, but it will provide cleaner speech data, data without need of specific voice filtering or removal. If the device 104 is recording a live conversation between the subject in-person with another, then the device 104 may be adapted to record only the speech of the subject (e.g., through collecting speech data using a wireless or wired headset and microphone). In other examples, all speech data from the call may be recorded, whether structured or unstructured, for all the subjects and then the desired subject speech data is filtered out for analysis. It is noted that the reference to speech data as used herein includes all voice related data for a subject, whether that voice data is in discernible speech or fragments of discernible speech, or other audible cues that can provide sufficient speech data for analysis. In any event, in examples where the machine 106 is integrated into existing wireless (or wired) phone networking equipment, then the monitoring and recording of the speech can be done at the machine 106, for example, in the extraction module 116. In other examples, as note, the machine 106 may be incorporated into the device 104

Through the feature extraction module 116 (blocks 210 and 212), the process 200 then performs the low-level and segment-level feature extraction on the second call data from block 208. For example, in reference to FIG. 3, speech data 300 from a second call is provided to the engine 116, where at the block 210, the engine performs initial low-level feature extraction using millisecond short-time measurements 302 (only some of which are labeled). Example low-level features include pitch of the speech data 302, the energy, spectrum, amplitude, zero crossing rate, voice activity level, and others mentioned herein or otherwise known.

Figure 3:
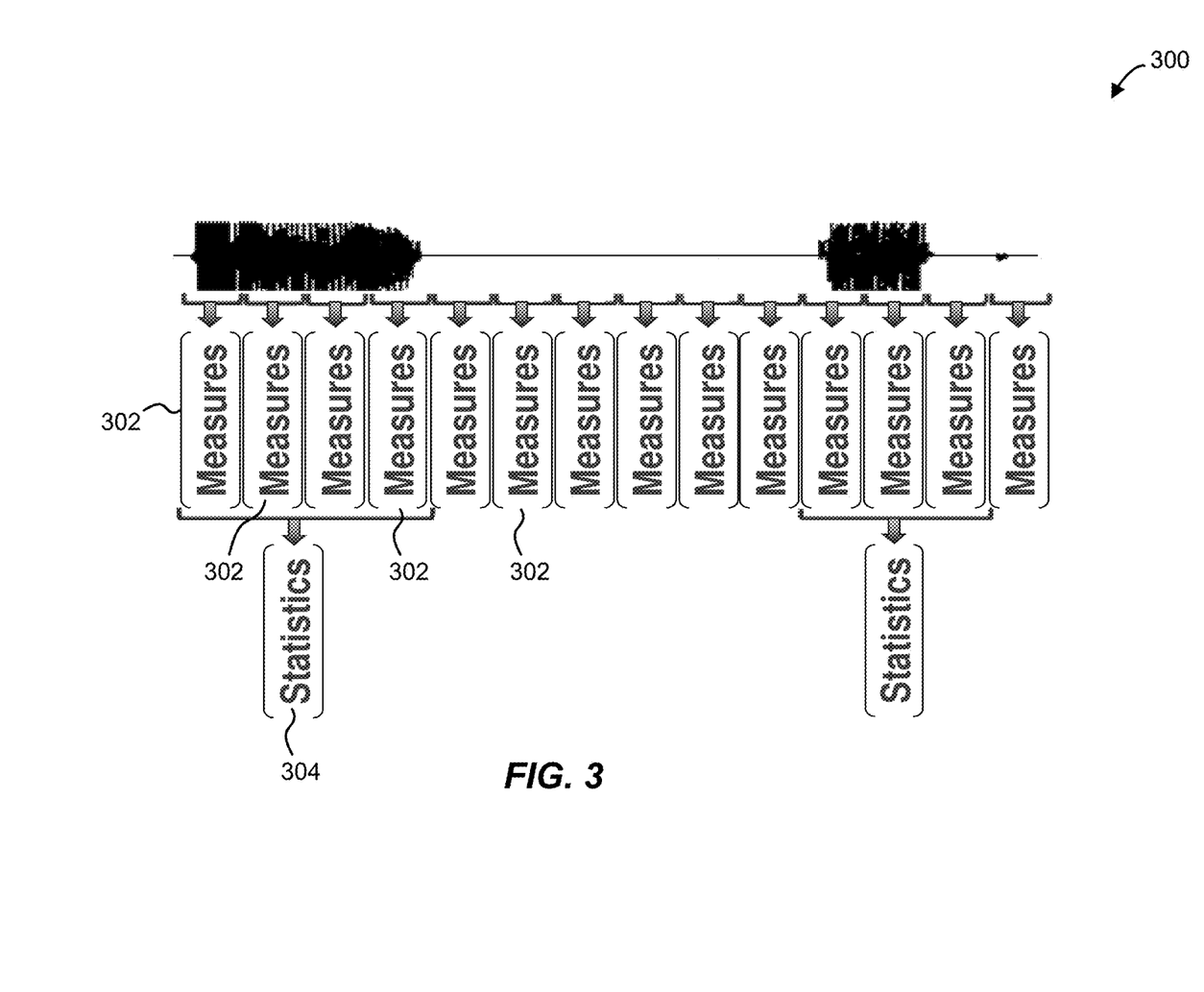
FIG. 3 illustrates example speech data that is used by the system of FIG. 1 in performing low-level feature extraction using millisecond time measurement filters for mood classification, in accordance with an example.

The feature extraction module 116 also performs segment-level (or statistical) feature extraction over a window of time 304, at a block 212. Example statistical feature extractions include long-time frame metrics include mean, variance, jitter, shimmer, entropy, kurtosis, any measure of fluctuations in the LLF over the window, and others mentioned herein or otherwise known. Other segment-level features include entropy, kurtosis, skew, or any other measures of fluctuations in the low-level features over the window. An advantage of this procedure of going from block 210 to 212 is that data is further privatized against lexical reconstruction. By performing low-level feature extraction at block 210 and then higher-level (statistical) feature extraction of that data, the process 200 does not examine raw speech data. The actual words used by the subject are essentially masked out by the blocks 210 and 212, in this particular implementation. In other examples, the processes herein may use feature extraction at the segment level that do not result from feature extraction at the low level, for example, by doing an analysis over an entire 3-30 second window.

The feature extraction module 116 provides the extracted segment-level (statistics or long-time) features data to the classification module 118, which along with the mood-state classification data from the ground truth assessment module 120, passes the data to a mood-state decision module 112. Both data may be transmitted in a training mode, when the device 116 is training its classification rules. Once the device 116 has classification rules in place these algorithms may be applied directly to extracted low-level and segment-level data received directly from the module 116, from received, unstructured speech data.

The mood state decision module (block 214) assesses the received data and develops classification rules, for example training a support vector machine (SVM) that, when applied to extracted speech data, automatically identifies, with a desired level of certainty, a determined mood state of the subject from the unstructured speech data. The resulting trained SVM classification rules are developed and stored at block 214 for later use by the machine 116.

Figure 4:
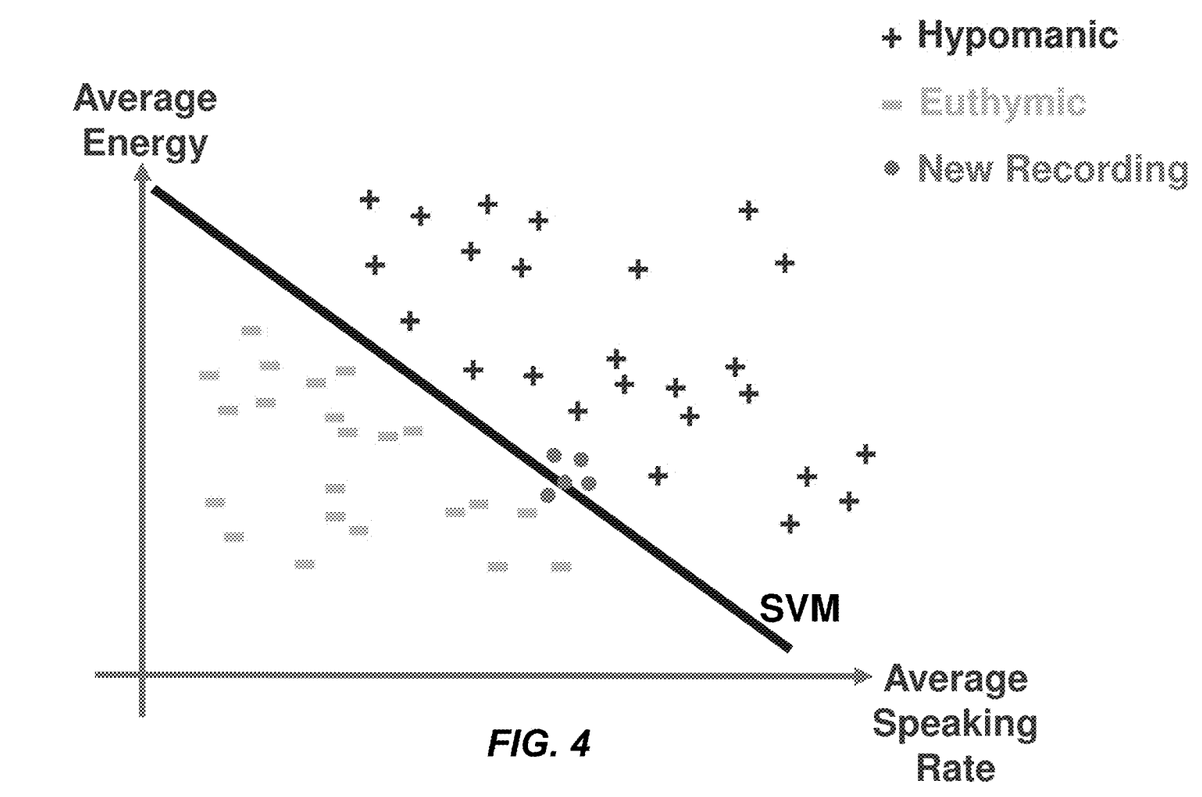
FIG. 4 is an illustration of a plot indicating an example classifier (i.e., classification rule) as determined by the system of FIG. 1 during a training procedure, in an example.

The term second call type includes a call type that is different than first. An example would be when the second call is an unstructured call, such as a normal call from the subject to a non-professional or not explicitly for the purposes of mood-state assessment. The term second call type, however, may include a second call that is of the same type as the first (i.e., where both are structure or unstructured). After the training procedure now described, any speech data from a subject (unstructured, structured, some combination thereof, etc.) may be analyzed by the machine 106 and trained mood-state decision module 122 may assess mood state. The trained classification rules are stored at a rules database 126. FIG. 4 illustrates an example SVM based classification rule, specifically for assessing hypomanic versus euthymic mood state, using statistical feature extractions of average energy and average speaking rate over a sample window.

Actual future mood determinations are made by the module 122 accessing the classification rules from database 126. Depending on the nature of the classification rules, and the desired certainty of their determinations, the module 122 may not only be able to assess current mood state but predict upcoming changes in mood state, as well.

The automatically determined mood state data may be communicated to the subject, health care professional, hospital administration system, pharmacy prescription system, insurance processing system, or other external system or entity. The mood state data may be communicated to family or personal support network. Additionally the mood state may be used to take action: for example schedule an appointment, ask the subject questions about sleep patterns and stress levels, launch an application designed to reduce mood-states, send email/SMS or notification suggestions reminding the subject to take medication sleep well eat well exercise.

It will be appreciated that the above descriptions are provided by way of example and that numerous modifications may be made within context of the present techniques.

More generally, the various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed:

1. A method of detecting a speech-identifiable condition of a subject, the method comprising:
   recording speech data of the subject via a communication device input that receives the speech data for the subject while not receiving speech data for anyone else talking to the subject;
   transmitting, by the communication device, the recorded speech data to a mood detection machine that includes a feature extraction module and a decision module;
   performing, in the feature extraction module, a low-level feature extraction on the speech data over a plurality of short-time segments to develop low-level feature data;
   performing, in the feature extraction module, a segment-level feature extraction on the low-level feature data over a window of time to develop segment-level feature data, where the window of time comprises the plurality of short time segments, and
   wherein the low-level feature extraction combined with the segment-level feature extraction masks out words contained in the speech data such that the segment-level feature data is non-lexical data;
   applying the segment-level feature data to the decision module that includes a database of one or more classifiers, each classifier from among the classifiers corresponding to a different classification of the speech-identifiable condition; and
   determining, in the decision module, the classification of the speech-identifiable condition of the subject from the segment-level feature data.

2. The method of claim 1, wherein the speech-identifiable condition is a mood state of the subject.

3. The method of claim 2, wherein the subject has bipolar disorder and the mood state comprises one or more of depression, hypomania/mania, and euthymia.

4. The method of claim 3, wherein the one or more classifiers comprises a classifier for identifying each of depression, hypomania/mania, and euthymia from the speech data.

5. The method of claim 1, wherein the speech data is unstructured speech data.

6. The method of claim 1, wherein the speech data is structured speech data.

7. The method of claim 1, wherein the low-level feature data includes one or more of pitch, energy, spectrum, zero-crossing rate, maximum waveform amplitude value, and minimum waveform amplitude value.

8. The method of claim 1, wherein the segment-level feature data includes one or more of mean, variance, jitter, and shimmer.

9. The method of claim 1, wherein each of the plurality of short time segments is 25 ms or less.

10. The method of claim 9, wherein the window of time is 3 s or greater.

11. The method of claim 10, wherein the window of time is from 3 s to 30 s.

12. The method of claim 1, wherein each of the one or more classification rules are support vector machine (SVMs).

13. The method of claim 12, further comprising:
   developing each of the one or more classifiers based on more than one of the segment-level data.

14. The method of claim 1, wherein determining, in the decision module, the classification of the speech-identifiable condition of the subject from the segment-level feature data comprises determining an expected future change in the speech-identifiable condition of the subject.

15. The method of claim 1, wherein the speech-identifiable condition includes one or more of psychiatrically diagnosed conditions, pain, depression, physical conditions, congenital heart disorders, coughing, lung related disorders, lung cancer, oncological disorders, Grave's disease, hearing impairment, neuromuscular disorders, and neurological disorders.

16. A mood detection machine to detect a speech-identifiable condition of a subject, comprising:
   a processor;
   a memory;
   a feature extraction module stored on the memory and adapted to cause the processor to:
      receive recorded speech data of the subject, the recorded speech data being transmitted by a communication device and recorded by an input of the communication device that receives the speech data for the subject while not receiving speech data for anyone else talking to the subject;
      perform, on the recorded speech data, a low-level feature extraction over a plurality of short-time segments to develop low-level feature data, and
      perform a segment-level feature extraction on the low-level feature data over a window of time to develop segment-level feature data, where the window of time comprises the plurality of short time segments contained therein,
      wherein the low-level feature extraction combined with the segment-level feature extraction masks out words contained in the recorded speech data such that the segment-level feature data is non-lexical data; and
   a decision module stored on the memory and adapted to cause the processor to:
      access a database of one or more classifiers, each classifier from among the classifiers corresponding to a different classification of the speech-identifiable condition; and determining the classification of the speech-identifiable condition of the subject from the segment-level feature data.

17. The mood detection machine of claim 16, wherein the segment-level feature data is non-lexical data.

18. The mood detection machine of claim 16, wherein the communication device is a cellular phone or a smart phone located remotely with respect to the mood detection machine, and wherein the communication device input is a microphone associated with the communication device.

19. The mood detection machine of claim 16, wherein the recorded speech data in unstructured speech data.

20. The method of claim 1, wherein the communication device is a cellular phone or a smart phone located remotely with respect to the mood detection machine, and wherein the communication device input is a microphone.

* * * * *

UNITED STATES PATENT AND TRADEMARK OFFICE
CERTIFICATE OF CORRECTION

PATENT NO. : 9,685,174 B2
APPLICATION NO. : 14/702215
DATED : June 20, 2017
INVENTOR(S) : Zahi N. Karam et al.

Page 1 of 1

It is certified that error appears in the above-identified patent and that said Letters Patent is hereby corrected as shown below:

In the Claims

At Column 16, Line 20, "classification rules" should be -- classifiers --.

At Column 16, Line 20, "machine" should be -- machines --.

At Column 17, Line 1, "determining" should be -- determine --.

At Column 19, Line 13, "in" should be -- is --.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*